United States Patent [19]

Nazarifar

[11] Patent Number: 5,676,530
[45] Date of Patent: Oct. 14, 1997

[54] SURGICAL CASSETTE LATCHING MECHANISM

[75] Inventor: Nader Nazarifar, Laguna Hills, Calif.

[73] Assignee: Alcon Laboratories, Inc., Fort Worth, Tex.

[21] Appl. No.: 590,655

[22] Filed: Jan. 24, 1996

[51] Int. Cl.⁶ .................................................. F04B 17/00
[52] U.S. Cl. ........................................ 417/360; 417/477.2
[58] Field of Search ........................... 604/153, DIG. 12; 417/360, 474, 477.2; 403/119, 113

[56] References Cited

U.S. PATENT DOCUMENTS

| | | | |
|---|---|---|---|
| 4,395,258 | 7/1983 | Wang et al. | 604/65 |
| 4,493,695 | 1/1985 | Cook | 604/27 |
| 4,627,833 | 12/1986 | Cook | 604/34 |
| 4,713,051 | 12/1987 | Steppe et al. | 604/30 |
| 4,758,238 | 7/1988 | Sundblom et al. | 604/319 |
| 4,790,816 | 12/1988 | Sundblom et al. | 604/31 |
| 4,798,580 | 1/1989 | DeMeo et al. | 604/30 |
| 5,267,956 | 12/1993 | Beuchat | 604/30 |
| 5,324,180 | 6/1994 | Zanger | 417/475 |
| 5,364,342 | 11/1994 | Beuchat et al. | 604/30 |

*Primary Examiner*—Timothy Thorpe
*Assistant Examiner*—Peter G. Korytnyk
*Attorney, Agent, or Firm*—Jeffrey S. Schira

[57] ABSTRACT

A cassette latching mechanism generally including an articulating clamp mounted on the end of a pneumatic cylinder. The clamp interacts with a slot, tab or tang on the cassette housing to hold the cassette firmly within a surgical console.

16 Claims, 5 Drawing Sheets

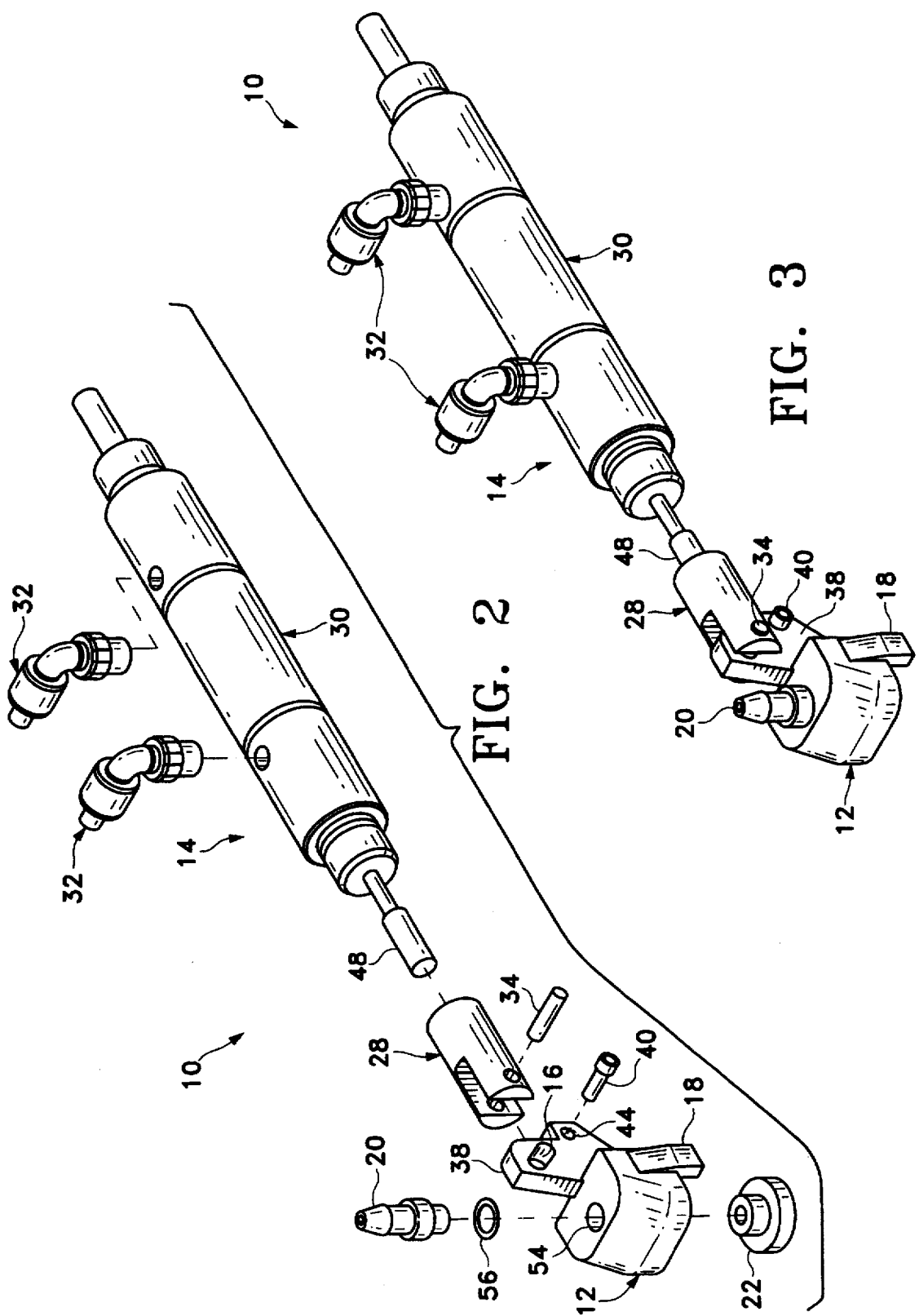

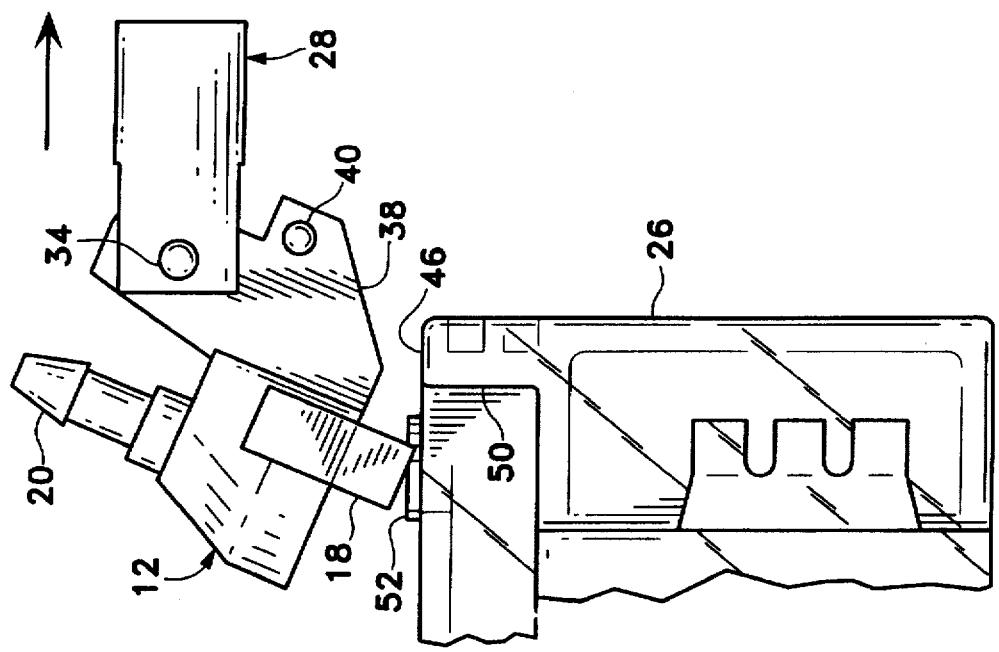
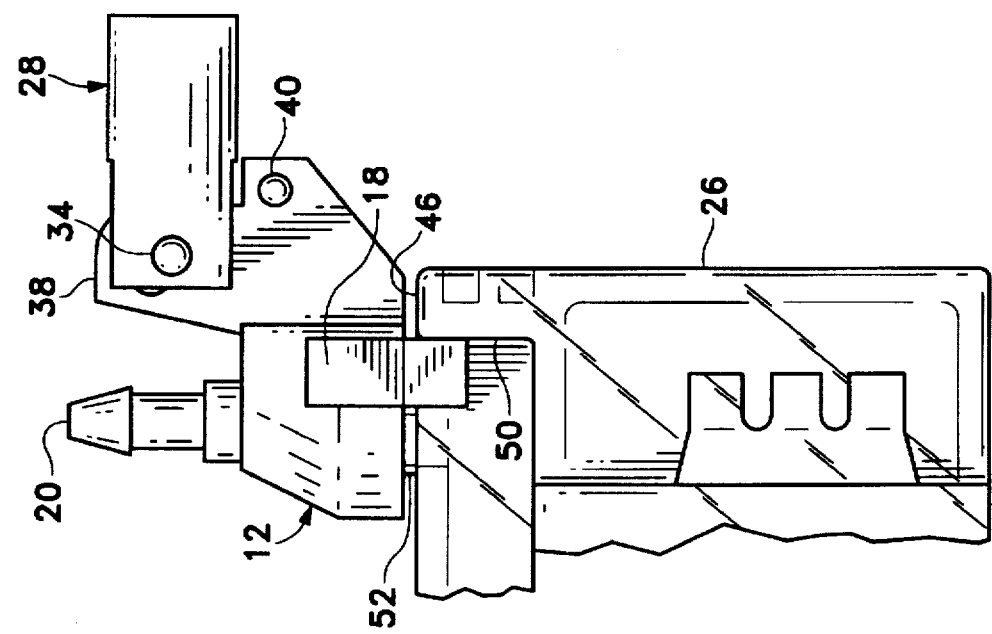

SURGICAL CASSETTE LATCHING MECHANISM

BACKGROUND OF THE INVENTION

The present invention relates to surgical cassettes and more particularly to a system for latching surgical cassettes.

The use of cassettes with surgical instruments to help manage irrigation and aspiration flows into a surgical site are well-known. U.S. Pat. Nos. 4,493,695, 4,627,833 (Cook), 4,395,258 (Wang, et al.), 4,713,051 (Steppe, et al.), 4,798,580 (DeMeo, et al.), 4,758,238, 4,790,816 (Sundblom, et al.) and 5,267,956, 5,364,342 (Beuchat) all disclose tubeless or tube-type surgical cassettes and are incorporated herein in their entirety by reference.

One of the primary function of the cassettes disclosed above is to control aspiration (vacuum) level at the surgical site. The vacuum generating device generally is contained within the surgical system control console and may be a venturi, diaphragm or peristaltic pump. Other mechanical interactions between the cassette and the console are also required, for example, to control fluid flow within the cassette and for monitoring the vacuum level within the cassette. These interaction require that the cassette be held securely within the console, with positive, aligned contact between the cassette and the console. Prior to the present invention, cassettes generally were secured within the console by a tight, friction fit or by a spring tab. These frictional methods of securing the cassette within the console can make the cassette difficult to insert and remove from the cassette from the console. In addition, these frictional methods do not positively lock the cassette within the console, so inadvertent removal of the cassette is possible.

Accordingly, a need exists for a mechanism to assist in latching a surgical cassette within a surgical console.

BRIEF DESCRIPTION OF THE INVENTION

The present invention generally includes an articulating clamp mounted on the end of a pneumatic or hydraulic cylinder. The clamp interacts with a slot, tab or tang on the cassette housing to hold the cassette firmly within a surgical console. The clamp articulates in response to extension or contraction of the cylinder to grasp securely the cassette tab and hold the cassette within the console.

Accordingly, one objective of the present invention is to provide a mechanism for latching a cassette within a surgical console.

Another objective of the present invention is to provide an articulating clamp that cooperates with a slot, tab or tang on a surgical cassette to hold the cassette firmly within a surgical console.

Still another objective of the present invention is to provide an articulating clamp mounted on the end of a cylinder that cooperates with a slot, tab or tang on a surgical cassette to hold the cassette firmly within a surgical console.

These and other objectives and advantages of the present invention will become apparent from the detailed description and claims which follow.

BRIEF DESCRIPTION OF THE DRAWINGS

FIG. 2 is an exploded perspective view of the articulating clamp and cylinder illustrated in FIG. 1.

FIG. 3 is a perspective view of the articulating clamp and cylinder similar to FIG. 2, but with the clamp assembled on the cylinder.

FIG. 8 is a partial side elevational view of the clamp of present invention cooperating with a recess in the surgical cassette illustrated in FIG. 1.

FIG. 9 is a partial side elevational view of the clamp of the present invention, similar to FIG. 8, but illustrating the clamp in the unclamped position.

DETAILED DESCRIPTION OF THE INVENTION

Figure 1:
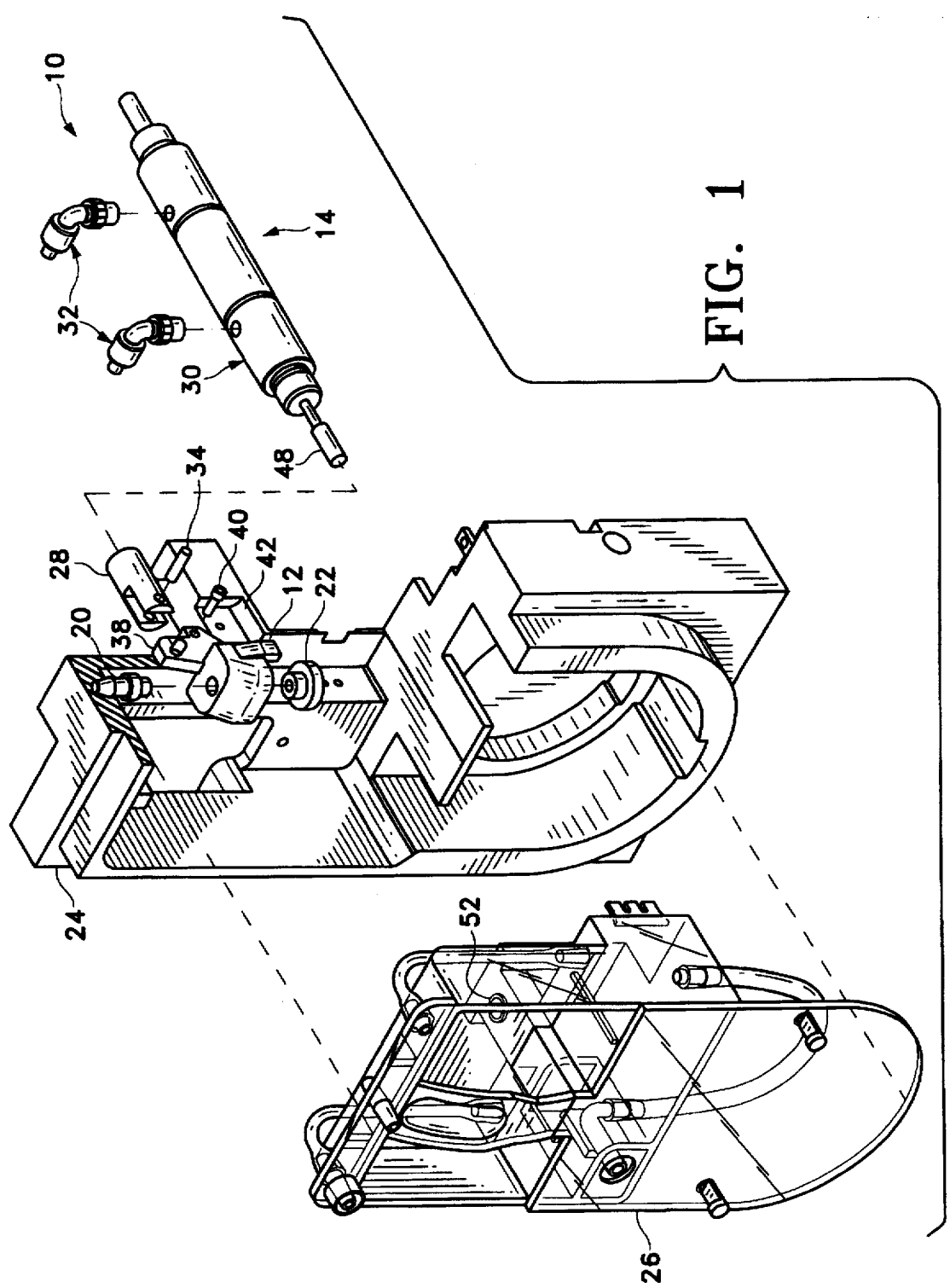
FIG. 1 is an exploded perspective view of the present invention and also illustrating one type of surgical cassette that can be used with the present invention.

As best seen in FIGS. 1–3, latching apparatus 10 of the present invention generally includes clamp 12 and cylinder 14. Clamp 12 may be of any suitable size and shape and includes passage 54, slotted mounting hole 16, prongs 18, flange 38 and fittings 20 and 22. Passage 54 and fittings 20 and 22 allow fluid communication between console 24 and cassette 26 through clamp 12. Clamp 12, prongs 18 and flange 38 preferably are made from steel, stainless steel, aluminum or titanium and formed in a single piece by machining, casting or forging. Fitting 22 preferably is formed of a resilient material such as silicone rubber or other equivalent elastomer and press fit into a recess (not shown) in clamp 12. Fitting 20 preferably is a slip fitting and made from steel, stainless steel, aluminum, titanium or suitable plastic. Fitting 20 may be mounted on clamp 12 by a press fit or threaded coupling and may include sealing washer 56.

Cylinder 14 may be any suitable pneumatic or hydraulic cylinder, such as pneumatic cylinder Model No. 56255-1173 manufactured by American Cylinder, and generally includes yoke 28, housing 30, rod 48, fittings 32 and pin 34. Yoke 28 is sized to cradle flange 38 on clamp 12 and may be threadably attached to rod 48. Flange 38 is held within yoke 28 by pin 34, which telescopes through slotted hole 16 so that pin 34 is frictionally held in yoke 28, but slides easily within slotted hole 16. Clamp 12 is attached to console 24 and held within recess 42 on console 24 by pin 40, which allows clamp 12 to pivot on pin 40 about hole 44 within recess 42, as shown in FIGS. 4–9. Yoke 28, housing 30, fittings 32 and pins 34 and 40 may be made of any suitable material such as brass, steel, stainless steel, aluminum or titanium.

Figure 4:
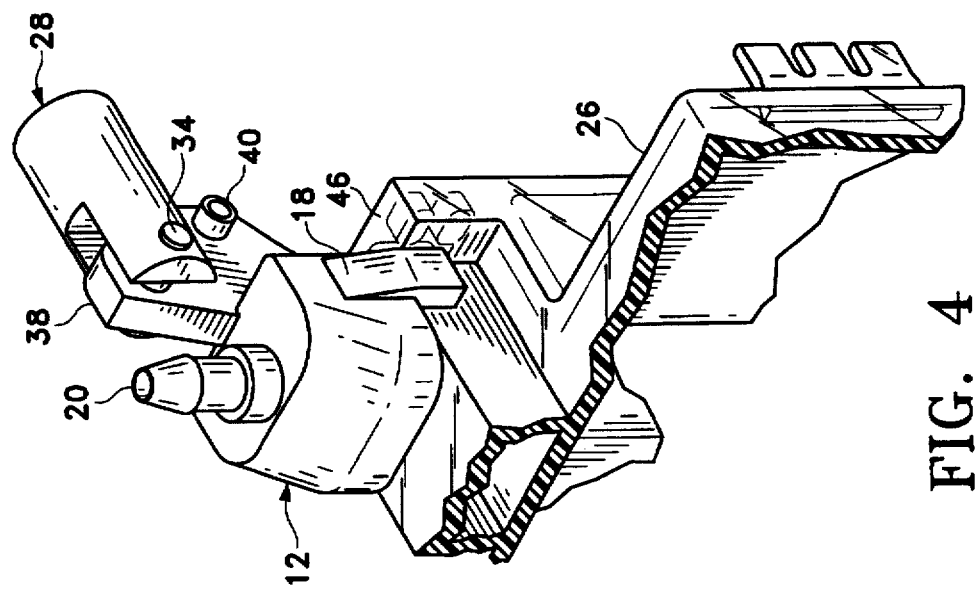
FIG. 4 is a perspective, partial cross-sectional view of the clamp of present invention cooperating with a recess in the surgical cassette illustrated in FIG. 1.
Figure 6:
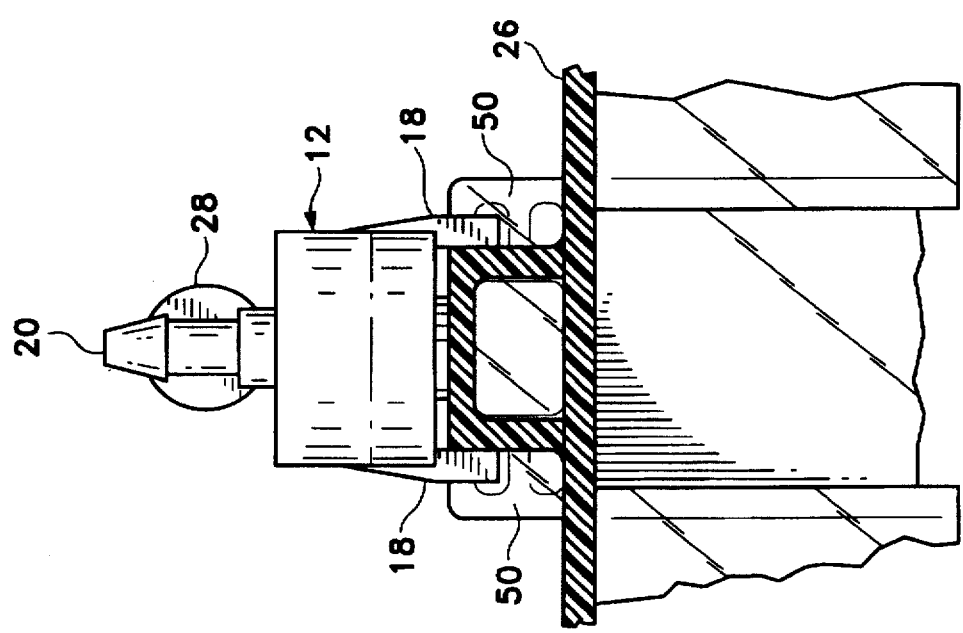
FIG. 6 is a front elevational, partial cross-sectional view of the clamp of present invention cooperating with a recess in the surgical cassette illustrated in FIG. 1.

As seen in FIGS. 4, 6 and 8, in its relaxed state, cylinder 14 is extended. Causing cylinder 14 to be extended in its relaxed state ensures that cassette 26 cannot be removed from console 24 if the power to console 24 is temporarily interrupted. When cylinder 30 is extended, rod 48 pushes yoke 28 forward, causing clamp 12 to pivot downward about pin 40 while pin 34 rides within slotted hole 16. The downward pivot of clamp 12 about pin 40 causes prongs 18 to rest below top edge 46 of cassette 26 and against recessed clamping faces 50 on cassette 26, thereby holding cassette 26 rigidly wig console 24. As best seen in FIGS. 6 and 8, when cassette 26 is held wig console 24, fitting 22 is held tightly against mating fitting 52 on cassette 26, allowing fitted communication with cassette 26 through fitting 22, passage 54 in clamp 12 and fitting 20. Cassette 26 may be any suitable surgical cassette having clamping faces 50 sized and shaped to receive prongs 18 on clamp 12.

Figure 5:
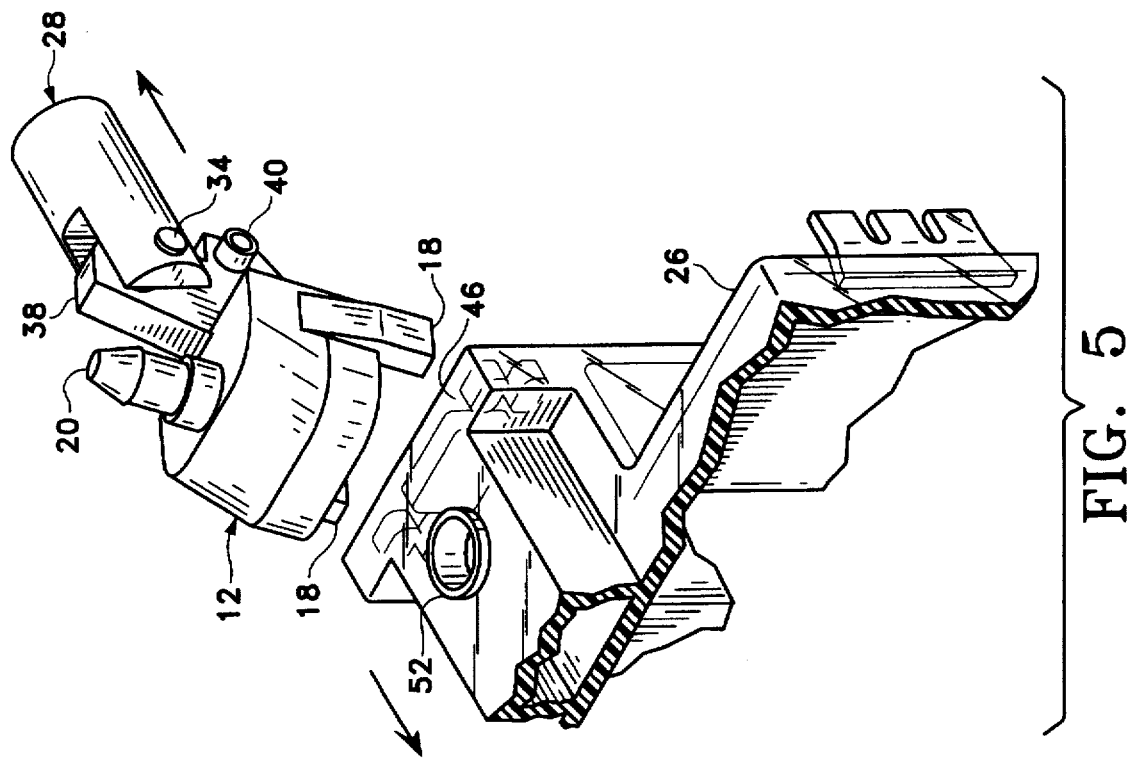
FIG. 5 is a perspective, partial cross-sectional view of the clamp of the present invention, similar to FIG. 4, but illustrating the movement of the clamp during clamping and unclamping of the cassette.
Figure 7:
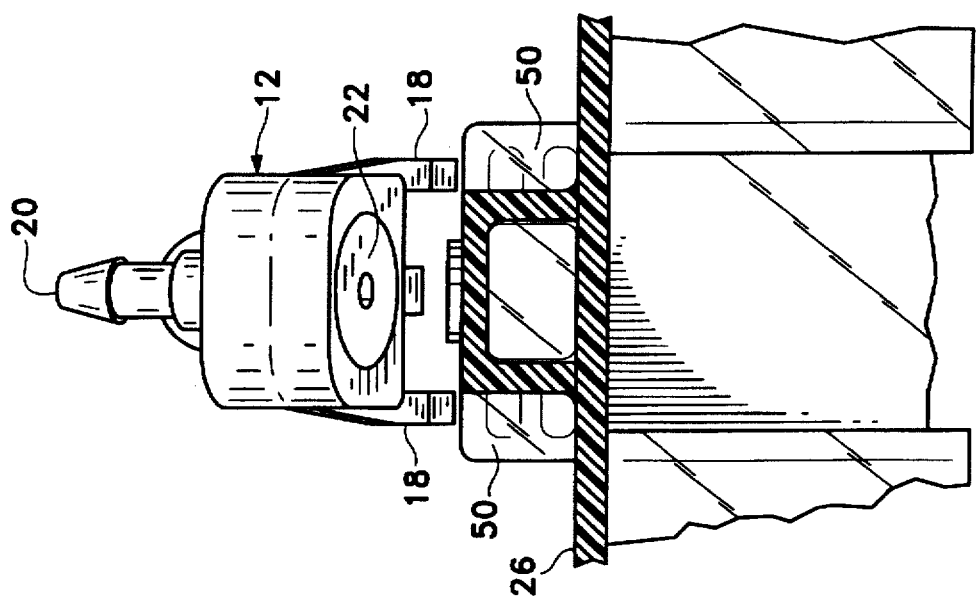
FIG. 7 is a front elevational, partial cross-sectional view of the clamp of the present invention, similar to FIG. 6, but illustrating the clamp in the unclamped position.

As seen in FIGS. 5, 7 and 9, to insert or remove cassette 26, a control means (not shown) within console 24 causes cylinder 14 to draw back on rod 48 and yoke 28, allowing clamp 12 to pivot about pin 40 while pin 34 rides within slotted hole 16. The pivoting action of clamp 12 allows prongs 18 to be raised about top edge 46 of cassette 26. In this position, cassette 26 may be easily removed or inserted.

This description is given for purposes of illustration and explanation. It will be apparent to those skilled in the relevant art that changes and modifications may be made to the invention described above without departing from its scope or spirit.

I claim:

1. An apparatus for latching a surgical cassette within a surgical console, comprising:
   a) an extendable cylinder mounted to the surgical console; and
   b) an articulating clamp having at least one prong, the clamp pivotally mounted to the cylinder and sufficiently close to the cassette so that the prong interacts with at least one clamping face on the surgical cassette when the cassette is inserted in the console so as to hold the cassette within the console.

2. The apparatus of claim 1 further comprising a fluid passage in the clamp.

3. The apparatus of claim 1 wherein the clamp has a flange and is mounted to the cylinder by a pin.

4. The apparatus of claim 1 wherein the clamp articulates about a pin held within a recess in the surgical console.

5. The apparatus of claim 1 wherein the cylinder comprises a pneumatic cylinder.

6. The apparatus of claim 1 wherein the cylinder comprises a hydraulic cylinder.

7. An apparatus for latching a surgical cassette within a surgical console, comprising:
   a) an extendable cylinder mounted to the surgical console; and
   b) an articulating clamp having a flange, a fluid passage and a plurality of prongs, the clamp pivotally mounted to the cylinder by a pin and located sufficiently close to the cassette when the cassette is inserted in the console so as to hold the cassette within the console.

8. The apparatus of claim 7 wherein the clamp articulates about a pin held within a recess in the surgical console.

9. The apparatus of claim 7 wherein the prongs cooperate with clamping faces on the surgical cassette.

10. The apparatus of claim 7 wherein the cylinder comprises a pneumatic cylinder.

11. The apparatus of claim 7 wherein the cylinder comprises a hydraulic cylinder.

12. An apparatus for latching a surgical cassette within a surgical console, comprising:
    a) an extendable cylinder mounted to the surgical console; and
    b) an articulating clamp having a plurality of prongs, the clamp pivotally mounted to the cylinder and sufficiently close to the cassette so that the prongs interact with a plurality of clamping faces on the surgical cassette when the cassette is inserted into the console and hold the cassette within the console.

13. The apparatus of claim 12 wherein the cylinder comprises a pneumatic cylinder.

14. The apparatus of claim 12 wherein the cylinder comprises a hydraulic cylinder.

15. The apparatus of claim 12 wherein the clamp has a flange and is mounted to the cylinder by a pin.

16. The apparatus of claim 12 further comprising a fluid passage in the clamp.

\* \* \* \* \*

UNITED STATES PATENT AND TRADEMARK OFFICE
CERTIFICATE OF CORRECTION

PATENT NO. : 5,676,530

DATED : October 14,1997

INVENTOR(S) : Nader Nazarifar

It is certified that error appears in the above-identified patent and that said Letters Patent is hereby corrected as shown below:

Col. 3, line 2
delete "wig"
and substitute therefore --within--.

Col. 3, line 3
delete "wig"
and substitute therefore --within--.

Signed and Sealed this

Fourteenth Day of July, 1998

Attest:

BRUCE LEHMAN

*Attesting Officer*  *Commissioner of Patents and Trademarks*